United States Patent [19]

Fogarty

[11] Patent Number: 4,566,446
[45] Date of Patent: Jan. 28, 1986

[54] PENILE PROSTHESIS DEVICE

[75] Inventor: Terence M. Fogarty, Lakeland, Minn.

[73] Assignee: Mentor Corporation, Minneapolis, Minn.

[21] Appl. No.: 483,184

[22] Filed: Apr. 8, 1983

[51] Int. Cl.⁴ .............................................. A61F 5/00
[52] U.S. Cl. ...................................... 128/79; 623/11; 623/26
[58] Field of Search ................. 128/79, 344, DIG. 25, 128/1 R, 70; 3/1; 604/217

[56] References Cited

U.S. PATENT DOCUMENTS

| | | | |
|---|---|---|---|
| 1,732,566 | 3/1928 | McKendrick | 604/317 |
| 3,495,589 | 2/1970 | Clement | 128/79 |
| 3,744,063 | 7/1973 | McWhorter et al. | 128/346 |
| 3,853,122 | 12/1974 | Strauch | 128/79 |
| 3,863,622 | 2/1975 | Buuck | 128/346 |
| 3,903,894 | 9/1975 | Rosen et al. | 128/346 |
| 3,954,102 | 5/1976 | Buuck | 128/79 |
| 4,009,711 | 3/1977 | Uson | 128/79 |
| 4,201,202 | 5/1980 | Finney et al. | 128/79 |
| 4,222,377 | 9/1980 | Burton | 128/346 |
| 4,224,934 | 9/1980 | Scott et al. | 128/79 |
| 4,235,227 | 11/1980 | Yamanaka | 128/79 |
| 4,267,829 | 5/1981 | Burton et al. | 128/79 |
| 4,318,396 | 3/1982 | Finney | 128/79 |
| 4,342,308 | 8/1982 | Trick | 128/79 |
| 4,353,360 | 10/1982 | Finney et al. | 128/79 |
| 4,364,379 | 12/1982 | Finney | 128/79 |
| 4,407,278 | 10/1983 | Burton et al. | 128/79 A |
| 4,449,520 | 5/1984 | Palomar | 128/79 |

FOREIGN PATENT DOCUMENTS

PCT/GB79/-
00130  8/1979  PCT Int'l Appl. .
1174814 12/1969  United Kingdom .

OTHER PUBLICATIONS

"An Implantable Fluid Transfer System for Treatment of Impotence," *Journal of Biomechanics*, vol. 5, pp. 557-570, Nov. 1972, by Kothari, Timm, Frohrib and Bradley.

"Management of Erectile Impotence, Use of Implantable Inflatable Prostheses," *Urology*, vol. II, No. 1, pp. 80-82, Jul. 1973 by Scott, Bradley and Timm.

"The Inflatable Penile Prosthesis by American Medical Systems", a brochure distributed by American Medical Systems, Inc., 3312 Gorham Avenue, Minneapolis, Minnesota 55426.

*Primary Examiner*—C. Fred Rosenbaum
*Assistant Examiner*—Mark Rooney
*Attorney, Agent, or Firm*—Kinney & Lange

[57] ABSTRACT

A penile prosthesis which is adapted for surgical implantation includes a pair of fluid fillable prosthetic members and a fluid reservoir containing a supply of the fluid. A pump pumps fluid from the reservoir to the prosthetic members. The pump includes a valving section which is fluidly connected with the reservoir and the prosthetic members, and a pumping section for pumping the fluid from the reservoir to the prosthetic members. The valving section includes a deformable housing with a supply inlet passage fluidly connected to the reservoir and two outlet passages, each outlet passage fluidly connected to a corresponding prosthetic member. Each passage has a check valve for directing the flow of fluid from the reservoir, through the pumping section and into the prosthetic members. When the valving section is manually deformed, the check valves are placed in an inoperable state permitting flow of the fluid from the prosthetic member, through the pumping section, and back into the reservoir.

12 Claims, 8 Drawing Figures

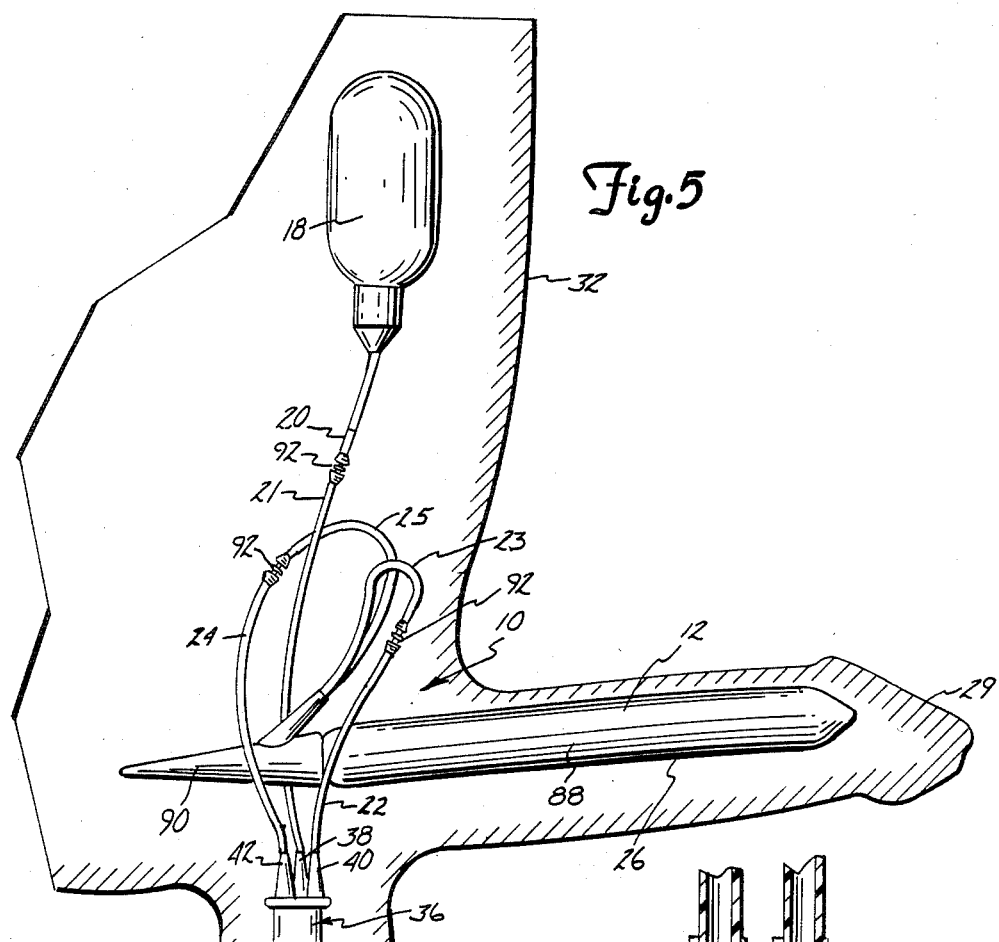
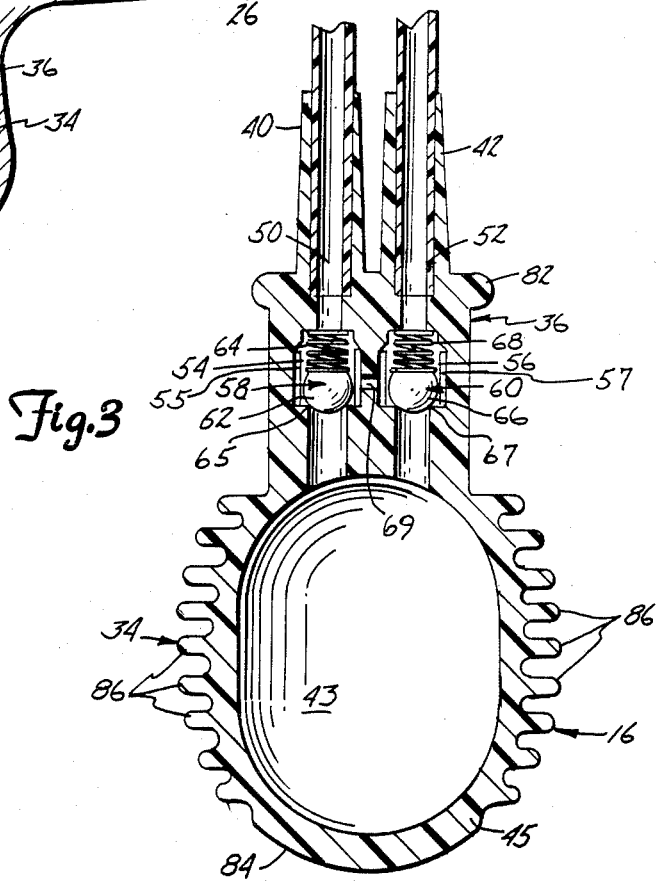

PENILE PROSTHESIS DEVICE

REFERENCE TO CO-PENDING APPLICATIONS

Reference is hereby made to the commonly assigned co-pending patent application filed on even date herewith entitled, "Connector Device for Connecting Elastic Tubing of an Implantable Device,"

BACKGROUND OF THE INVENTION

1. Field of the Invention

The present invention relates to implantable penile prostheses, and in particular, it relates to penile prostheses which are selectively filled with a fluid by a pumping arrangement from a supply reservoir.

2. Description of the Prior Art

Sexual impotence caused by failure to achieve erection of the penis is a common problem. When the impotence is organic in origin, surgeons have attempted to duplicate the function of the erectile tissue (corpora cavernosa) in the penis by way of a surgically implanted prosthesis. The function of the prosthesis is to provide an artificial erection.

One type of prosthesis presently being used is a hydraulic type of prosthesis having generally tubular-shaped prosthetic members with extensible walls for implantation in the corpora cavernosa. The prosthesis is inflated by using a fluid drawn from a reservoir. As the prosthesis is inflated, the penis changes from a flaccid state to an erect state, mimicing normal erection. There are several prior art hydraulic prostheses for implantation in the corpora cavernosa. Several types of hydraulic prostheses are described in the following patents: Strauch et al U.S. Pat. No. 3,853,122, Uson U.S. Pat. No. 4,009,711, Finney et al U.S. Pat. No. 4,201,202, Yamanaka U.S. Pat. No. 4,235,227, Scott et al U.S. Pat. No. 4,224,934, Burton et al U.S. Pat. No. 4,267,829 and the Finney U.S. Pat. Nos. 4,318,396; 4,353,360 and 4,360,010. In addition, a PCT international published application submitted by Said Hakky having publication number WO 80/00302 shows a hydraulic prosthesis. The above mentioned patents disclose an implantable penile prosthesis having hydraulic prosthetis members that are supplied a fluid from a reservoir. The reservoir is made from a flexible material and is squeezed to pump fluid to enlarge the prosthetic members.

Two articles entitled "An Implantable Fluid Transfer System for Treatment of Impotence," in the *Journal of Biomechanics* by Kothari, Timm, Frohrib and Bradley, Vol. 5, November, 1972, pp. 567–570 and "Management of Erecticle Impotence, Use of Implantable Penile Prosthesis," in *Urology* by Scott, Bradley and Timm, Vol. II, No. 1, July 1973, pp. 80–82, describe a hydraulic penile prosthesis having two prosthetic members, a reservoir, a first squeezable bulb for pumping fluid from a reservoir into the prosthetic member, and a second squeezable bulb for pumping fluid from the prosthetic member back to the reservoir. The prosthesis described in the Kothari et al and the Scott et al articles, although a refinement of the manner of supplying fluid to the prosthetic member over previous devices, has a disadvantage that the user must differentiate between the first bulb and the second bulb through the skin.

The Buuck U.S. Pat. No. 3,954,102 describes a prosthesis having a pair of hydraulic prosthetic members, an elastomeric bulb implantable in the scrotal sac for inflating and deflating the prosthetic member and a reservoir. The bulb is squeezed through the user's skin to pump fluid from the reservoir to the prosthetic member. To deflate the prosthetic member, the device includes a bypass valve arrangement. The bypass valve arrangement has a ball that is seated at both ends so that a sealing action normally exists within the elastomeric bulb permitting pumping of the fluid from the reservoir to the prosthetic member. When the device is squeezed in the location of the bypass ball, the ball is unseated, permitting the fluid to bypass both check valves and return to the reservoir, deflating the prosthetic member. However, the device of the Buuck Patent is difficult to use since generally the pumping portion of the bulb is difficult to distinguish from the bypass portion by feel through the user's skin.

SUMMARY OF THE INVENTION

The present invention includes a penile prosthesis device having fluid fillable prosthetic members for implantation in the corpora cavernosa. Fluid to the prosthetic members is supplied from a reservoir through a pump that pumps fluid from the reservoir to the prosthetic members. The pump includes a valving section that is fluidly connected with the reservoir and the prosthetic members, and a pumping section for pumping the fluid from the reservoir to the prosthetic members. The valving section includes a flexible deformable housing having a supply inlet passage and two outlet passages. The two outlet passages are each fluidly connected to a corresponding prosthetic member. The passages each have a check valve for directing fluid flow from the reservoir, through the pumping section, and into the prosthetic member. When the valving section is manually deformed, the fluid is permitted to flow back from the prosthetic member through the pumping section and into the reservoir.

In a preferred embodiment, a flange is positioned proximate the valving section with a diameter greater than the diameter of the valving section. The user can easily find the valving section through the skin of the scrotal sac by locating the flange.

In another preferred embodiment, the inlet and outlet passages of the valving section are disposed in a substantially triangular configuration separated from each other by an integral wall structure that is integral with the housing of the valving section. The outlet passages are fluidly connected in the valving section by an aperture disposed such that when one check valve of the outlet passages is unseated, fluid flows from both prosthetic members through the unseated check valve. The triangular configuration of the passages results in the inlet and at least one outlet passage check valve being unseated regardless of the direction of deformation of the valving section. The aperture permits fluid to flow from the prosthetic member whose check valve was not unseated through the unseated check valve.

BRIEF DESCRIPTION OF THE DRAWINGS

FIG. 3 is a cross sectional view of the pump of the prosthesis device of the present invention taken along the line 3—3 in FIG. 2;

FIG. 5 is a perspective view of the inflatable prosthesis device of the present invention implanted in a human body with the inflatable prosthetic members in an erect position;

DETAILED DESCRIPTION OF THE PREFERRED EMBODIMENT

Figure 1:
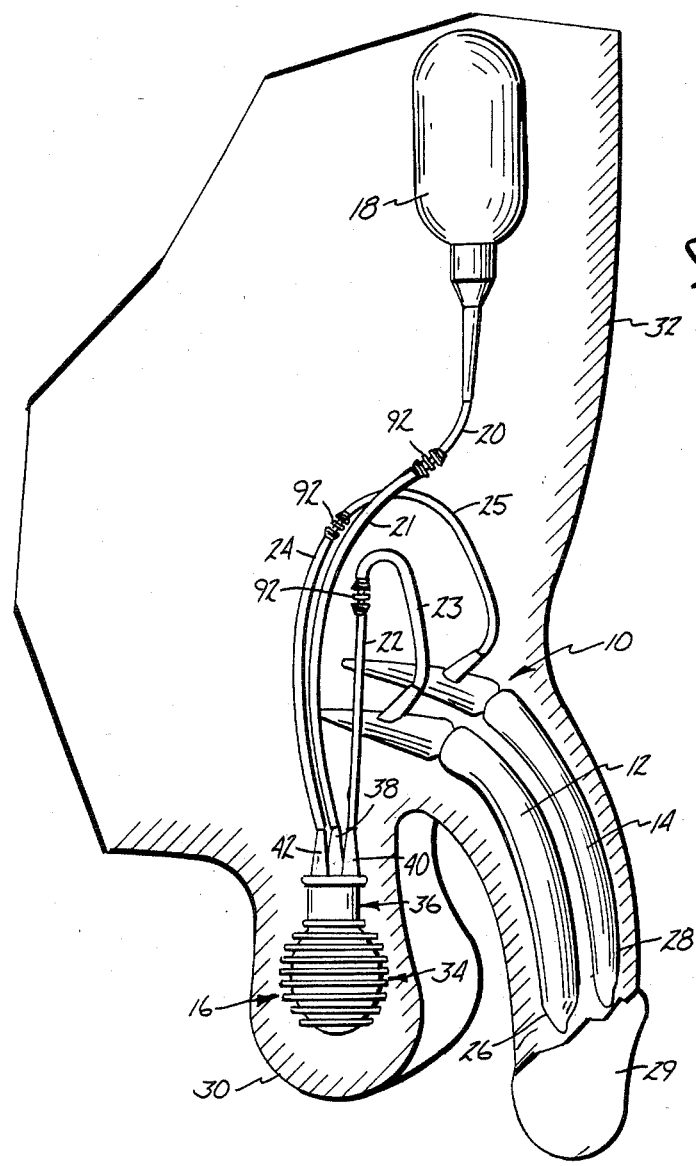
FIG. 1 is a perspective view of the inflatable prosthesis device of the present invention implanted in a human with portions of the human body cut away for purposes of clarity.

The implantable penile prosthesis of the present invention is generally indicated at 10 in FIG. 1. The penile prosthesis includes two prosthetic members 12 and 14, a pump 16, and a fluid reservoir 18. Flexible tubing 20, 21 fluidly connect the fluid reservoir 18 with the pump 16; flexible tubing 22, 23 fluidly connect the prosthetic member 12 with the pump 16; and flexible tubing 24, 25 fluidly connect the prosthetic member 14 with the pump 16.

As illustrated in FIG. 1, the implantable penile prosthesis of the present invention is adapted for implantation in a male for the treatment of erectile impotence. The prosthetic members 12 and 14 are implanted within dialated corpora cavernosa 26 and 28, respectively, of a penis 29. The pump 16 is implanted in a scrotal sac 30 and the reservoir 18 is positioned above the prosthetic members 12 and 14 behind an abdominal wall 32.

The implantable prosthesis of the present invention provides an artificial erection to an impotent male. The pump 16 located in the scrotal sac 30 is squeezed manually by the user pumping fluid into the prosthetic members 12 and 14 distending and enlarging the member 12 and 14 causing an erection.

The fluid reservoir 18 is a flexible container made from a medical grade polymeric elastomer. The fluid reservoir 18 is filled with preferably a noncompressible liquid for use in inflating the prosthetic members 12 and 14.

The tubing 20, 21 fluidly connect the fluid reservoir 18 to the pump 16 by providing a suitable passage for the fluid between the pump 16 and the fluid reservoir 18. The tubing 20, 21 are made of a suitable medical grade polymeric elastomer, such as a silicone polymer.

The pump 16, as illustrated in FIG. 1, includes a pumping section 34 and a valving section 36. The valving section 36 includes a fluid supply inlet 38 and fluid outlets 40 and 42. Preferably, the entire pump 16 is also made of a medical grade polymeric elastomer.

Figure 2:
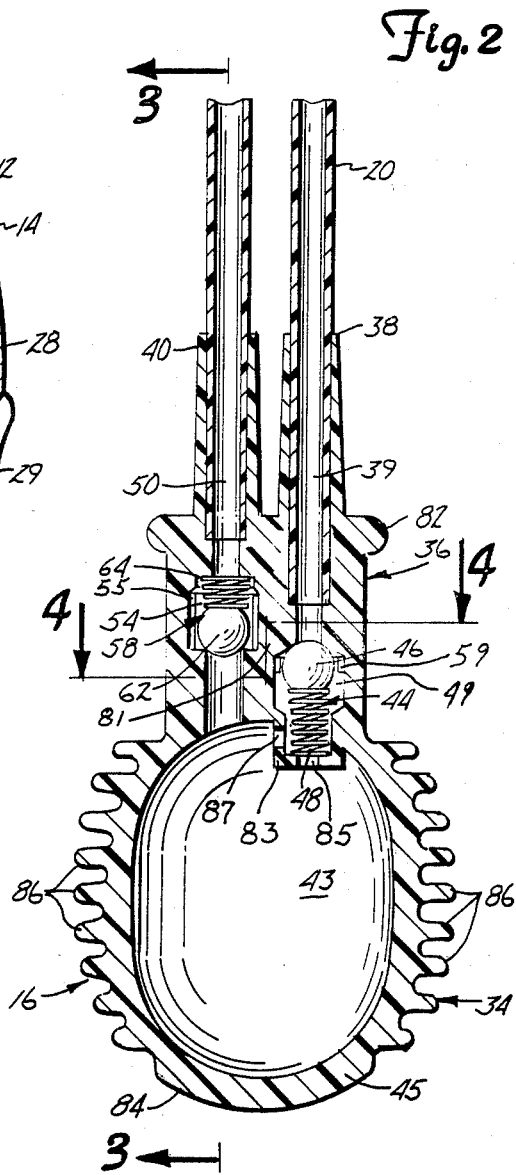
FIG. 2 is a cross sectional view of the pump of the prosthesis device of the present invention taken along the line 2—2 in FIG. 4.

Referring to FIG. 2, wherein the pump 16 is shown in an enlarged sectional view, the pumping section 34 is illustrated in a generally bulb-shaped configuration. The pumping section 34 includes an interior chamber 43 whose function is to hold fluid supplied from the reservoir 18. The pumping section 34 includes a flexible wall 45 that is designed to be squeezed manually forcing fluid out of the interior chamber 43 through the tubing 22, 23 and 24, 25 to the prosthetic members 12 and 14.

Positioned on top of the pumping section 34 and in fluid communication therewith is the valving section 36. The valving section 36 controls the flow of the fluid from the reservoir 18 to the prosthetic members 12 and 14 and back from the members 12 and 14 to the reservoir 18.

The supply inlet 38 has a fluid passage 39 that communicates with the interior chamber 43 of the pumping section 34. A check valve 44 is situated within an enlarged cavity 49 in the passage 39, and includes a check ball 46 biased by a coil spring 48 in a direction toward the fluid reservoir 18. The check ball 46 is biased against a surface of the cavity 49 such that the flow of fluid through the passage 39 is stopped when the pumping section is squeezed.

The outlets 40, 42 fluidly communicate with the interior chamber 54 and have fluid passages 50, 52, respectively, as illustrated in FIG. 3. In each fluid passage 50, 52, is an enlarged cavity 54, 56, respectively, containing check valves 58, 60. The check valve 58 includes a check ball 62 biased by a coil spring 64 against a surface 65. Similarly, the check valve 60 has a check ball 66 biased by a coil spring 68 against a surface 67. An aperture 69 is disposed to fluidly connect the cavities 54 and 56 on a side of the check valves 58, 60 toward the prosthetic members. The check valves 58 and 60 are biased in a direction to prevent flow of the fluid from the prosthetic members 12, 14 to the chamber 43 when the pump 16 is not being used. In one successful embodiment, check valves 58 and 60 provide a minimum of 3 psi backpressure to prevent undesired filling of the prosthetic members.

As should be noted from FIG. 2, the coil spring 48 does not provide as great a biasing force as the other coil springs 64, 68 of check valves 58, 60. The biasing force of the coil spring 48 is sufficient to keep the check ball 46 in a seated position while permitting the check ball 46 to move to an unseated position when the pumping section 34 needs fluid.

As illustrated in FIG. 3, the cavity 54 and 56 have a plurality of inwardly projecting ribs 55 and 57, respectively. The ribs 55 and 57 extend along the entire length of the chamber to contain the springs 64, 68 and the check balls 62 and 66, respectively. In one successful embodiment, the cavities 54 and 56 have eight ribs equally spaced-apart from each other along the surface of the cavity.

Similarly, the cavity 49 has a plurality of inwardly projecting ribs 59 which extend along the cavity sufficiently to contain only the check ball 46. The spring 48 is lightly loaded and containment by the ribs would frictionally interfere with the action of the spring 48.

Figure 4:
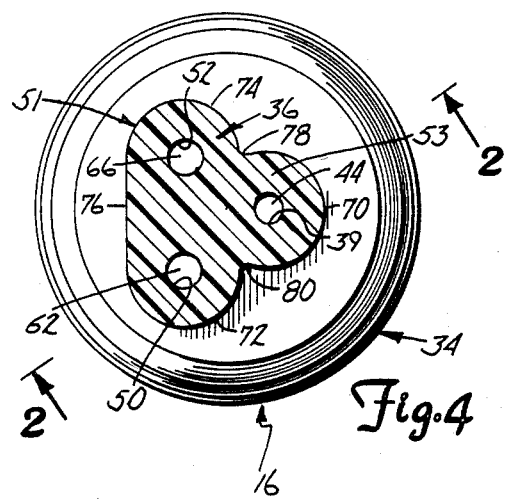
FIG. 4 is a cross sectional view of the valving section of the pumping device taken along the line 4—4 in FIG. 2.

The valving section 36 is sufficiently narrower in diameter than the generally bulb-shaped pumping section 34 to permit the user to easily distinguish between the valving section and the pumping section through the scrotal sac wall. In the valving section, the passages 39, 50 and 52 are spaced from each other in a triangular configuration and separated from each other by flexible walls formed by the body of the valving section, as illustrated in FIG. 4. The passages 39, 50 and 52 are enclosed by a continuous outer wall 53 having an exterior surface 51 of a unique configuration. A portion 70 of the exterior surface 51 partially surrounding passage 39 has a cylindrical configuration. Similarly, exterior surface portions 72 and 74 partially surrounding passages 50, 52, respectively, are also cylindrical in configuration. The cylindrical surface portions 72 and 74 merge to form a substantially flat surface portion 76 proximate the passages 52 and 50 on one side of the valving section 36. On an opposite side of the valving section 36, the cylindrical surface portions 72 and 74 merge with the cylindrical surface portion 70 forming concave surface portions 78, 80, respectively.

The check valves 44, 58 and 60 are seated substantially along the same plane, as illustrated in FIG. 2. The check balls 46, 62 and 66 are positioned equidistant from a central axis of the valving section and disposed approximately 120° about the central axis. The check valve 44, as illustrated in FIG. 2, is positioned from the check valves 58 and 60 on an opposite side of the plane common to the check valve seats. The immediately above-mentioned arrangement results in a common flexible wall portion 81.

To deflate the prosthetic members 12 and 14, the valving section 36 is grasped manually anywhere along the outer surface of the valving section. Disturbing the check ball 46 will unseat either check balls 62 or 66 through common flexible wall portion 81. With both passages 54 and 56 being fluidly connected through aperture 69, both prosthetic members will deflate by the fluid flowing through the aperture 69 and the unseated check ball through the interior chamber 43 of the pumping section and through the passage 49 containing the unseated inlet check valve 44. Disturbing either one of the check balls 62 or 66 will unseat the check ball 46 deflating the prosthetic members in a similar manner. In addition, deformation of any of the flexible walls separating the passages 39, 50 and 52 from each other will unseat the check valve 44 and either one of the check valves 58 or 60, deflating the prosthetic members as immediately above-described. The substantially flat surface portion 76 insures that the check valve 44 is unseated with at least one of the check valves 58 or 60.

The spring 48 of the check valve 44 is positioned in a portion 83 of the valving section that extends into the interior chamber 43 of the pumping section. A fluid opening 85 normally allows fluid to flow through the passage 49 to and from the reservoir and the interior chamber 43 of the pumping section. A second fluid opening 87 is provided proximate an upper wall of the interior chamber 43. If the opening 85 becomes closed during squeezing of the pumping section, fluid will be permitted to flow to and from the prosthetic members through the opening 87.

The valving section 36 preferably includes a flange-type lip 82 extending beyond the exterior surface 51 on a side of the valving section opposite from the pumping section 34. The flange-type lip 82 and the generally bulb-shaped pumping section 34 define upper and lower limits of the valving section 36 permitting easy location of the valving section by the user even though positioned within the scrotal sac.

The pumping section 34 has an exterior surface 84 having a plurality of circular ridges 86 projecting outwardly. When the pump 16 is implanted in the scrotal sac 30, the ridges 86 prevent the pump from slipping out of the user's grasp by frictionally engaging an inner wall of the scrotal sac. The ridges 86 permit the user to continuously squeeze the pump 16, inflating the members 12 and 14, without the pump slipping from the user's grasp during pumping.

The prosthetic members 12 and 14 are best described with reference to FIG. 5, wherein only prosthetic member 12 is shown in a distended and enlarged state. The prosthetic member 12 includes a controlled distensible portion 88 and a nondistensible portion 90 fluidly connected with each other forming one fluid retaining member. The nondistensible portion 90 is preferably made of a silicone, although other materials such as polyurethane are acceptable. The distensible portion is preferably polyurethane. The prosthetic members 12 and 14 have a generally tubular configuration suitable for implantation in the corpora cavernosa.

Figure 6:
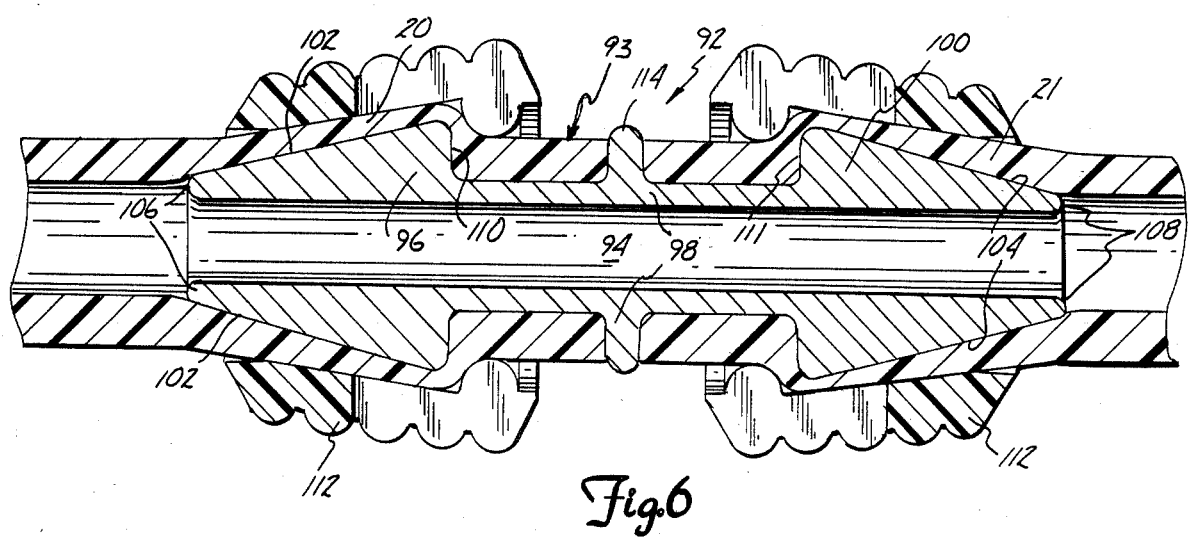
FIG. 6 is an enlarged cross sectional view of the connector for connecting the tubing of the prosthesis device of the present invention.

The tubing 23 and 25 is fixedly attached at one end to the nondistensible portion 90 of each of the prosthetic members 12 and 14, respectively. The other tubing sections 22 and 24 are also fixedly attached to the fluid outlets 42 and 40 of the pump 16, respectively. Similarly, the tubing 20 is fixedly attached to the fluid reservoir 18 at one end and the tubing 21 is fixedly attached to the supply inlet of the pump 16 at one end. A connector 92 fluidly connects the tubing 22 and 23, 24 and 25, and 20 and 21, as best seen in enlarged cross sectional view in FIG. 6. For purposes of discussion, the connector 92 is shown with tubing 20 and 21 but it should be understood that the connector 92 is used to connect all the tubing in the present invention. The connector 92 is described in detail in an application entitled "Connector Device for Connecting Elastic Tubing of an Implantable Device" filed on even date with the present application and which is herein incorporated by reference.

Briefly, the connector 92 includes a rigid connector component 93 and a pair of clamps 112. The rigid connector component includes a fluid passage 94 that permits fluid to pass between the tubing sections 20 and 21. The connector 92 of the present invention permits the tubing to be slid onto the connector easily without puncturing or piercing the tubing and holds tubing sections in fluid connection over an extended period of time. The connector component 93 has a first tubing retaining section 96, a center section 98, and a second tubing retaining section 100. The tubing retaining sections 96 and 100 have frusto-conical surfaces 102, 104, respectively. The frusto-conical surfaces 102 and 104 permit the elastic tubing to be slid easily over the tubing retaining sections 96 and 100. In addition, the tubing retaining sections 96 and 100 have end wall surfaces 106, 108, respectively, that are rounded with a radius equal to one-half the thickness of the retaining section at the end wall surface. The rounded end surfaces 106 and 108 not only facilitate the positioning of the tubing over the tubing retaining sections 96, 100, but eliminate the problem of the tubing being pierced while the device of the present invention is being assembled.

The frusto-conical surfaces 102, 104 increase in diameter towards the center section 98 until the diameter of the frusto-conical surfaces is greater than the diameter of the center section 98. The point of difference in diameter between the frustoconical surfaces and the center section 98 is defined by drop-off surfaces 110, 111. The center section 98 preferably includes an annular flange 114 which serves as a separation and a stop between the tubing sections 20 and 21.

The tubing sections 20 and 21 are held in position by the tubing clamps 112. The clamps 112 provide compressive forces in a lateral and longitudinal direction when positioned over the tubing to retain the tubing on the connector component in a connected state over an extended period of time.

Figure 7:
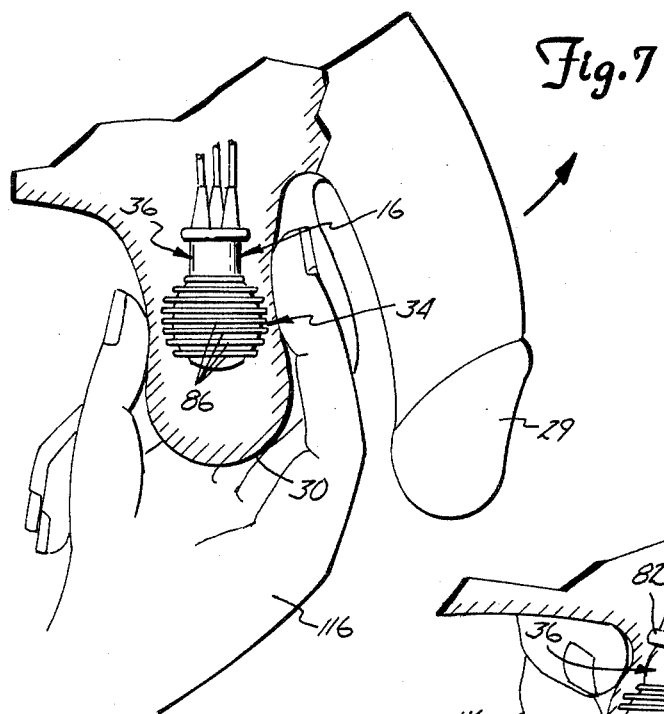
FIG. 7 is a perspective view illustrating the manner of pumping fluid to the inflatable prosthetic members.

The penile prosthesis of the present invention mimics the natural erection process. When the penile prosthesis has been implanted, a penile erection is produced by grasping the scrotal sac 30 with a hand 116, as illustrated in FIG. 7, and squeezing the pumping section 34 of the pump 16 through the scrotal sac wall. In this step, the ridges 86 of the pumping section prevent the pumping section 34 from slipping out off the user's grasp during pumping, eliminating the discomfort experienced is using prior art prosthetic devices.

By squeezing the pump 16, fluid is transferred from the reservoir 18 through the tubing 20, 21 and into the prosthetic members 12 and 14 causing a penile erection, as illustrated in FIG. 5.

Figure 8:
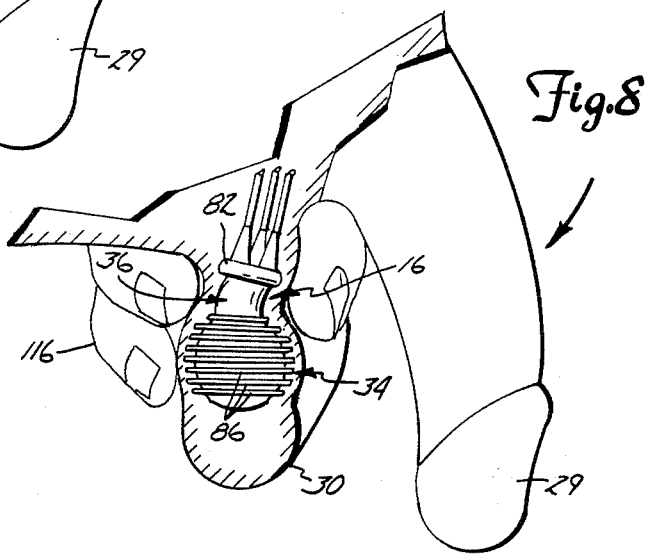
FIG. 8 is a perspective view showing the manner of deflating the prosthetic members.

To return the penis 19 from an erect to a flaccid position, the valving section 36 is grasped by the hand 116 and deformed, as illustrated in FIG. 8. The inlet check valve and at least one outlet check valve are unseated regardless of the point of deformation of valving section due to the structure of the valving section. When the check valves are unseated, fluid flows from the prosthetic members 12 and 14 through the pumping section 34 and back into the reservoir 18. The flange-type lip 82 and the generally bulb-shaped pumping section 34 permit the user to easily find the valving section through the scrotal sac walls.

Although the present invention has been described with reference to preferred embodiments, workers skilled in the art will recognize that changes may be made in form and detail without departing from the spirit and scope of the invention.

What is claimed is:

1. A prosthetic penile device comprising:
   fluid fillable penile prosthetic means;
   a fluid reservoir for storing a fluid;
   means for pumping fluid from the reservoir to the prosthetic means including a housing having a longitudinal axis and having a valving section defined along the longitudinal axis for controlling fluid flow between the fluid reservoir and the prosthetic means, the housing of the valving section being made of a flexible deformable material with a fluid supply inlet having a fluid inlet passage fluidly connected to the fluid reservoir and first and second fluid outlets fluidly connected to the prosthetic members, each outlet having a fluid outlet passage, the fluid inlet and the outlets having check valve means disposed in the fluid passages, the fluid passages of the inlet and outlets being disposed from each other in a substantially triangular configuration in cross-section substantially perpendicular to the longitudinal axis, and a pumping section fluidly communicating with the valving section for pumping the fluid from the reservoir to the prosthetic means, the valving section when in a normal position with the check valve means properly seated permitting fluid flow only from the reservoir, through the pumping section to the prosthetic means, and when in an inoperable position with the check valve means of the fluid inlet and at least one fluid outlet unseated by deformation of the valving section, permitting fluid to flow back to the reservoir from the prosthetic means through the pumping section and the check valve means;
   first conduit means for fluidly connecting the reservoir and the means for pumping; and
   second conduit means for fluidly connecting the means for pumping and the prosthetic means.

2. The device of claim 1 wherein the fluid fillable penile prosthetic means includes first and second fluid fillable prosthetic members fluidly connected to the first and second fluid outlets, respectively, by the second conduit means.

3. The device of claim 1 wherein the check valve means are disposed approximately 120° from each other about the longitudinal axis of the valving section.

4. The device of claim 3 wherein the housing of the valving section has an outer surface including first and second cylindrical surface portions partially surrounding the first and second fluid passages, respectively, and a substantially flat surface portion extending between the first and second cylindrical surface portions and a third cylindrical surface portion partially surrounding the inlet passage converging with the first and second cylindrical surface portions forming first and second concave surface portions, respectively.

5. The device of claim 1 wherein the check valve means in the first and second outlets include a check ball and a biasing spring biasing the check ball against a flexible seat in each fluid outlet passage in a direction preventing fluid from escaping from the prosthetic means.

6. The device of claim 1 wherein the fluid outlet passages are fluidly connected with each other on a side of the check valve means toward the prosthetic means.

7. The device of claim 6 wherein the check valve means in the inlet includes a check ball and a biasing spring biasing the check ball against a flexible seat in the fluid inlet passage in a direction toward the fluid reservoir.

8. The device of claim 7 wherein the seats of the check valve means in the outlet passages and the inlet passage lie along a substantially common plane.

9. The device of claim 1 wherein the pumping section is a generally bulb-shaped flexible chamber.

10. The device of claim 9 wherein the generally bulb-shaped chamber has a plurality of exterior projections on an exterior surface.

11. The device of claim 10 wherein the projections are spaced-apart rings extending outwardly from the exterior surface.

12. The device of claim 1 and further including a flange-type lip positioned on one side of the valving section opposite from the pumping section and wherein the lip and the pumping section are both sufficiently greater in diameter than the valving section to permit easy location of the valving section through the scrotal sac.

* * * * *